US00PP19543P2

(12) United States Plant Patent
Hammond

(10) Patent No.: US PP19,543 P2
(45) Date of Patent: Dec. 2, 2008

(54) ***ARGYRANTHEMUM* PLANT NAMED 'HH140'**

(50) Latin Name: *Argyranthemum frutescens*
Varietal Denomination: HH140

(75) Inventor: Francis William Hammond, Narre Warren East (AU)

(73) Assignee: Amerinova Properties LLC, Bonsall, CA (US)

( * ) Notice: Subject to any disclaimer, the term of this patent is extended or adjusted under 35 U.S.C. 154(b) by 0 days.

(21) Appl. No.: 11/978,498

(22) Filed: Oct. 29, 2007

(51) Int. Cl.
*A01H 5/00* (2006.01)

(52) U.S. Cl. ..... Plt./406

(58) Field of Classification Search ..... Plt./406
See application file for complete search history.

*Primary Examiner*—Kent L Bell
(74) *Attorney, Agent, or Firm*—C. A. Whealy

(57) ABSTRACT

A new and distinct cultivar of *Argyranthemum* plant named 'HH140', characterized by its compact, outwardly spreading and mounded plant habit; freely branching growth habit; freely flowering habit; single-type inflorescences with ray florets that are initially yellow in color becoming pink with development; and good garden performance.

1 Drawing Sheet

Botanical designation: *Argyranthemum frutescens.*
Cultivar denomination: 'HH140'.

BACKGROUND OF THE INVENTION

The present invention relates to a new and distinct cultivar of *Argyranthemum* plant, botanically known as *Argyranthemum frutescens* and hereinafter referred to by the name 'HH140'.

The new *Argyranthemum* is a product of a planned breeding program conducted by the Inventor in Narre Warren East, Victoria, Australia. The objective of the breeding program is to create new compact *Argyranthemum* cultivars with unique and attractive ray floret coloration.

The new *Argyranthemum* originated from an open-pollination in 1999 in Narre Warren East, Victoria, Australia of the *Argyranthemum frutescens* cultivar M512, not patented, as the female, or seed, parent with an unknown selection of *Argyranthemum frutescens,* as the male, or pollen, parent. The new *Argyranthemum* was discovered and selected by the Inventor as a single flowering plant within the progeny of the stated open-pollination in a controlled environment in Narre Warren East, Victoria, Australia in March, 2000.

Asexual reproduction of the new *Argyranthemum* by vegetative cuttings in a controlled environment in Narre Warren East, Victoria, Australia since September, 2000 has shown that the unique features of this new *Argyranthemum* are stable and reproduced true to type in successive generations.

SUMMARY OF THE INVENTION

Plants of the cultivar HH140 have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'HH140'. These characteristics in combination distinguish 'HH140' as a new and distinct potted *Argyranthemum* cultivar:

1. Compact, outwardly spreading and mounded plant habit.
2. Freely branching growth habit.
3. Freely flowering habit.
4. Single-type inflorescences with ray florets that are initially yellow in color becoming pink with development.
5. Good garden performance.

Plants of the new *Argyranthemum* differ from plants of the female parent, the cultivar M512 in the following characteristics:

1. Plants of the new *Argyranthemum* are larger than plants of the cultivar M512.
2. Ray florets of plants of the new *Argyranthemum* are initially yellow in color becoming pink with development whereas ray florets of plants of the cultivar M512 are pink in color.

Plants of the new *Argyranthemum* can be compared to plants of the *Argyranthemum* cultivar Crème, not patented. In side-by-side comparisons conducted in Narre Warren East, Victoria, Australia, plants of the new *Argyranthemum* differed from plants of the cultivar Créme primarily in ray floret color as plants of the cultivar Crème had yellow-colored ray florets.

BRIEF DESCRIPTION OF THE PHOTOGRAPHS

The accompanying photographs illustrate the overall appearance of the new *Argyranthemum.* These photographs show the colors as true as it is reasonably possible to obtain in colored reproductions of this type. Colors in the photographs may differ slightly from the color values cited in the detailed botanical description which accurately describe the colors of the new *Argyranthemum.*

The photograph at the bottom of the sheet comprises a side perspective view of a typical flowering plant of 'HH140' grown in a container.

The photograph at the top of the sheet is a close-up view of typical inflorescences of 'HH140'.

DETAILED BOTANICAL DESCRIPTION

The aforementioned photographs and following observations and measurements describe plants grown in an outdoor nursery during the spring in Bonsall, Calif. and under conditions and practices which approximate those generally used in commercial *Argyranthemum* production. During the production of the plants, day temperatures ranged from about 4° C. to about 35° C. and night temperatures ranged from about 1° C. to 18° C. Plants were pinched one time. Plants used in the photographs and for the description were about seven weeks old. In the following description, color references are made to The Royal Horticultural Society Colour Chart, 1995 Edition, except where general terms of ordinary dictionary significance are used.

Botanical classification: *Argyranthemum frutescens* cultivar HH140.

Parentage:

*Female, or seed, parent.*—*Argyranthemum frutescens* cultivar M512, not patented.

*Male, or pollen, parent.*—Unknown selection of *Argyranthemum frutescens,* not patented.

Propagation:

*Type.*—Vegetative cuttings.

*Time to initiate roots, summer.*—About 10 days at temperatures of 25° C.

*Time to initiate roots, winter.*—About 15 days at temperatures of 20° C.

*Time to produce a rooted young plants, summer.*—About 15 days at temperatures of 25° C.

*Time to produce a rooted young plants, winter.*—About 20 days at temperatures of 20° C.

*Root description.*—Fibrous, medium thickness; white in color.

*Rooting habit.*—Moderate branching; moderately dense.

Plant description:

*Appearance.*—Herbaceous single-type potted *Argyranthemum*. Compact, outwardly spreading and mounded plant habit. Strong and freely branching growth habit with five to six lateral branches and secondary branches potentially developing at every node; dense and full plants. Vigorous growth habit.

*Plant height.*—About 18.5 cm.

*Plant width.*—About 26 cm.

*Lateral branches.*—Length: About 16 cm. Diameter: About 4 mm. Internode length: About 7 mm. Strength: Strong. Texture: Smooth, glabrous. Color: 147B.

Foliage description:

*Arrangement.*—Opposite, simple.

*Length.*—About 3.6 cm.

*Width.*—About 2.8 cm.

*Shape.*—Deeply dissected with five lobes.

*Apex.*—Acute.

*Base.*—Attenuate.

*Margin.*—Pinnatifid; entire.

*Texture, upper and lower surfaces.*—Smooth, glabrous.

*Venation pattern.*—Pinnate.

*Color.*—Developing foliage, upper surface: 146B. Developing foliage, lower surface: 146C. Fully expanded foliage, upper surface: 147A; venation, 147B. Fully expanded foliage, lower surface: 147B; venation, 147B.

*Petiole length.*—About 1.5 cm.

*Petiole diameter.*—About 2.5 mm.

*Petiole texture, upper and lower surfaces.*—Smooth, glabrous.

*Petiole color, upper surface.*—147B

*Petiole color, lower surface.*—146A. .

Inflorescence description:

*Appearance.*—Single-type inflorescence form with ligulate-shaped ray florets. Inflorescences borne on terminal and axillary peduncles above foliage. Disk and ray florets arranged acropetally on a capitulum.

*Fragrance.*—None detected.

*Flowering season.*—Plants flower from spring to fall in Southern California; flowering continuous during this period.

*Inflorescence longevity.*—Inflorescences last about ten days on the plant; inflorescences persistent.

*Quantity of inflorescences.*—Freely flowering, about 40 inflorescences develop per plant.

*Inflorescence bud.*—Height: About 1 cm. Diameter: About 7 mm. Shape: Ovoid. Color: 11C.

*Inflorescence size.*—Diameter: About 3.4 cm. Depth (height): About 9 mm. Diameter of disc: About 1.3 cm. Receptacle height: About 6 mm. Receptacle diameter: About 1.1 cm. Receptacle color: 147C.

*Ray florets.*—Shape: Ligulate. Orientation: Initially upright, then perpendicular to the peduncle. Length: About 1.4 cm. Width: About 4 mm. Apex: Emarginate. Base: Acute. Margin: Entire. Texture, upper and lower surfaces: Smooth, glabrous. Number of ray florets per inflorescence: About 25 arranged in a single whorl. Color: When opening, upper surface: 10C. When opening, lower surface: 11C. Fully opened, upper surface: 10D; color shifting to 75A to 75B with development, towards the base, 11B. Fully opened, lower surface: 11D; color becoming closer to 11D tinted with 69A with development.

*Disc florets.*—Arrangement: Massed at center of receptacle. Shape: Tubular, enlarged. Apex: Five-pointed. Length: About 6 mm. Width, at apex: About 1.5 mm. Width, at base: About 1 mm. Number of disc florets per inflorescence: About 140. Color, immature: Apex: 153C. Mid-section: 21B. Base: 157A. Color, mature: Apex: 14B. Mid-section: 157A. Base: 157D.

*Phyllaries.*—Number of phyllaries per inflorescence: About 28 in three or four whorls. Length: About 4 mm. Width: About 2 mm. Shape: Elliptic. Apex: Broadly acute. Base: Truncate. Margin: Entire. Texture, upper surface: Smooth, glabrous. Texture, lower surface: Pubescent. Color, upper surface: 147C. Color, lower surface: 146C.

*Peduncles.*—Length, terminal peduncle: About 4.7 cm to 5.2 cm. Length, fourth peduncle: About 5.4 cm. Diameter: About 1 mm. Angle: Erect to about 40° to 45° from vertical. Strength: Moderately strong, flexible. Texture: Smooth, glabrous. Color: 146C.

*Reproductive organs.*—Androecium: Quantity per disc floret: Five. Filament length: About 1.5 mm. Filament color: 157D. Anther shape: Rounded. Anther length: Less than 1 mm. Anther color: 23A. Pollen amount: Scarce. Pollen color: 23A. Gynoecium: Pistil length: About 7 mm. Stigma shape: Two-parted. Stigma color: 15A. Style length: About 3 mm. Style color: 145D. Ovary color: 145D.

*Seed/fruit.*—Seed and fruit production has not been observed.

Disease/pest resistance: Resistance to pathogens and pests common to *Argyranthemums* has not been observed on plants grown under commercial conditions.

Garden performance: Plants of the new *Argyranthemum* have been observed to have good garden performance and to tolerate wind, rain and temperatures from about 1° C. to about 40° C.

It is claimed:

1. A new and distinct *Argyranthemum* plant named 'HH140' as illustrated and described.

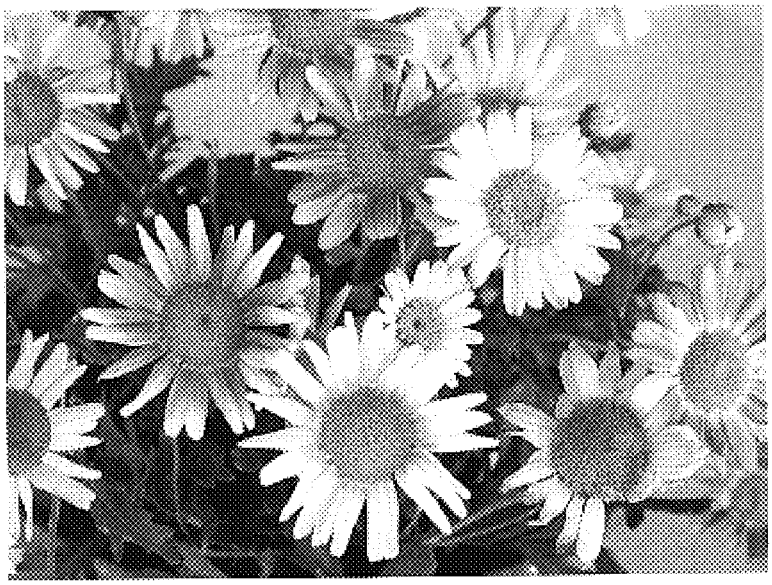
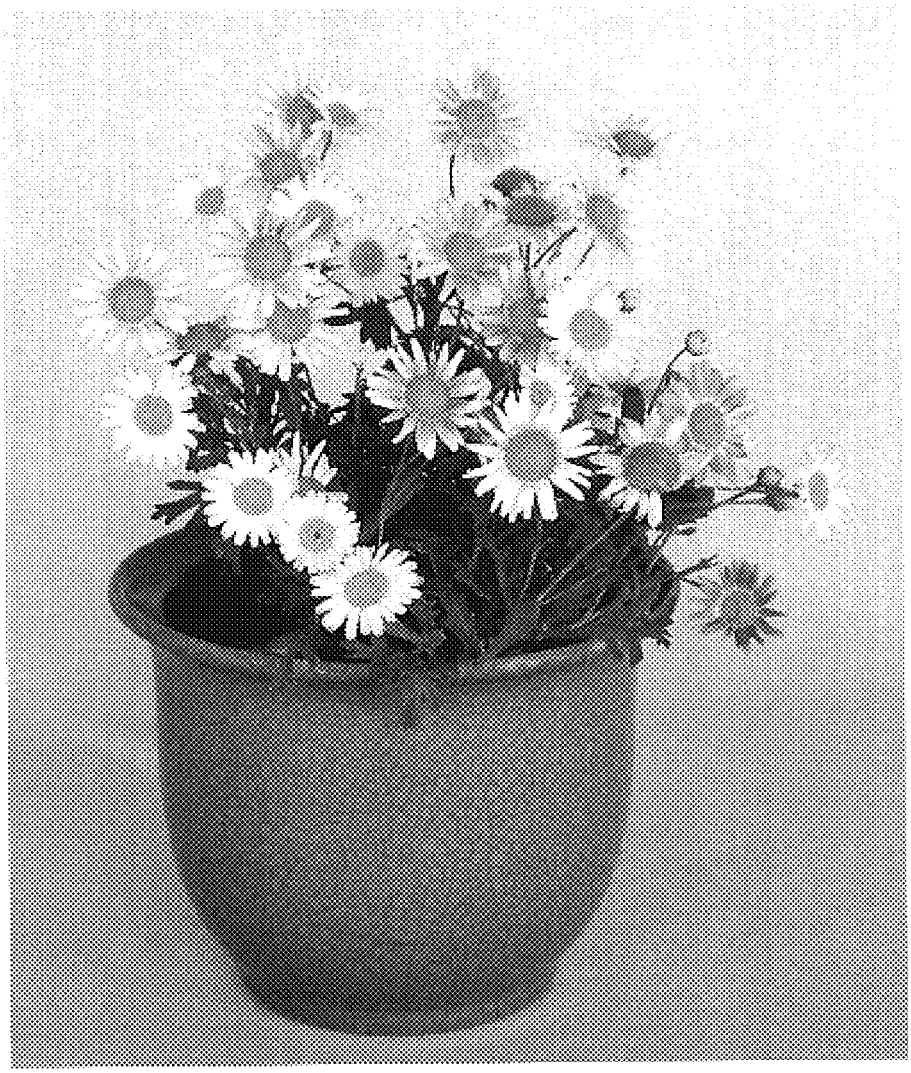

* * * * *